(12) United States Patent
Zhang

(10) Patent No.: US 7,442,397 B2
(45) Date of Patent: Oct. 28, 2008

(54) PEGYLATED FIBRINOGEN-BASED BIOMATRIX

(75) Inventor: Jianyi Zhang, Roseville, MN (US)

(73) Assignee: Regents of the University of Minnesota, Saint Paul, MN (US)

(*) Notice: Subject to any disclaimer, the term of this patent is extended or adjusted under 35 U.S.C. 154(b) by 241 days.

(21) Appl. No.: 10/874,449

(22) Filed: Jun. 23, 2004

(65) Prior Publication Data
US 2005/0118144 A1 Jun. 2, 2005

Related U.S. Application Data

(63) Continuation-in-part of application No. PCT/US03/13697, filed on May 1, 2003.

(60) Provisional application No. 60/377,148, filed on May 2, 2002, provisional application No. 60/382,985, filed on May 24, 2002.

(51) Int. Cl.
*A61K 35/28* (2006.01)
*C12N 5/08* (2006.01)
*C12N 5/02* (2006.01)

(52) U.S. Cl. ............... 426/577; 435/372; 435/374; 435/405

(58) Field of Classification Search ................... None
See application file for complete search history.

(56) References Cited

U.S. PATENT DOCUMENTS

| | | | |
|---|---|---|---|
| 5,197,985 | A | 3/1993 | Caplan et al. |
| 5,486,359 | A | 1/1996 | Caplan et al. |
| 5,766,584 | A | 6/1998 | Edelman et al. |
| 6,099,832 | A | 8/2000 | Mickle et al. |
| 6,110,459 | A | 8/2000 | Mickle et al. |
| 6,174,333 | B1 | 1/2001 | Kadiyala et al. |
| 6,261,549 | B1 | 7/2001 | Fernandez et al. |
| 6,420,339 | B1 | 7/2002 | Gegg et al. |
| 6,552,170 | B1 | 4/2003 | Thompson et al. |

FOREIGN PATENT DOCUMENTS

| | | |
|---|---|---|
| WO | WO 96/00782 | 1/1996 |
| WO | WO 96/27397 | 9/1996 |
| WO | WO 99/03973 | 1/1999 |
| WO | WO 99/18931 | 4/1999 |
| WO | WO 03/041568 | 5/2003 |
| WO | WO 03/093433 | * 11/2003 |

OTHER PUBLICATIONS

"9. Can Stem Cells Repair A Damaged Heart?" printed from internet http://stemcells.nih.gov/info/scireport/PDFs/chapter9.pdf, 2001, pp. 87-92.
"Stem Cell Expert to Deliver Stowell Lecture at UC Davis," News From UC Davis Health System printed from internet http://news.ucdmc.ucdavis.edu/stowell_Lecture.html, Oct. 16, 2001, 2 pages.
Gronthos et al., "The STRO-1+ Fraction of Adult Human Bone Marrow Contains the Osteogenic Precursors," *Blood*, 1994, 84(12):4164-4173.
Horch et al., "Single-cell suspensions of cultured human keratinocytes in fibrin-glue reconstitute the epidermis," *Cell Transplant*, 1998, 7(3):309-317.
Jackson et al., "Regeneration of ischemic cardiac muscle and vascular endothelium by adult stem cells," *J. Clin. Invest.*, 2001, 107(11):1395-1402.
Lillge, "The Case for *Adult* Stem Cell Research," 21st Century Science & Technology Magazine, Winter 2001-2002 at http://21stcenturysciencetech.com/articles/winter01/stem_cell.html, 6 pages.
Makino et al., "Cardiomyocytes can be generated from marrow stromal cells in vitro," *J. Clin. Invest.*, 1999, 103(5):697-705.
Murakami et al., "Myocardial creatine kinase kinetics in hearts with postinfarction left ventricular remodeling," *Am. J. Physiol.*, 1999, 276:H892-H900.
Murakami et al., "Myocardial Oxygenation During High Work States in Hearts With Postinfarction Remodeling," *Circulation*, 1999, 99:942-948.
Pittenger et al., "Multilineage Potential of Adult Human Mesenchymal Stem Cells," *Science*, 1999, 284:143-147.
Springer et al., "Not the usual suspects: the unexpected sources of tissue regeneration," *J. Clin. Invest.*, 2001, 107(11):1355-1356.
Toma et al., "Human Mesenchymal Stem Cells Differentiate to a Cardiomyocyte Phenotype in the Adult Murine Heart," *Circulation*, 2002, 105:93-98.
Watanabe et al., "Cardiomyocyte Transplantation in a Porcine Myocardial Infarction Model," *Cell Transplantation*, 1998, 7(3):239-246.
Zhang and Bache, "The Molecular Energetics of the Failing Heart from Animal Models—Large Animal Models," *Heart Failure Reviews*, 1999, 4:255-267.
Zhang et al., "Functional and Bioenergetic Consequences of Postinfarction Left Ventricular Remodeling in a New Porcine Model," *Circulation*, 1996, 94:1089-1100.
Zhang, "Experimental Biology 2001 Symposium Mitochondria and Energy Metabolism in Heart Failure, Hypertrophy and Remodeling: Myocardial Energetics In Cardiac Hypertrophy," *Clin. Exp. Pharmacol. Physiol.*, 2002, 29:351-359.

* cited by examiner

*Primary Examiner*—Michail Belyavskyi
(74) *Attorney, Agent, or Firm*—Fish & Richardson P.C.

(57) ABSTRACT

The invention involves methods and materials related to fibrin-based biomatrices.

10 Claims, 10 Drawing Sheets

CD-44

CD-45

HLA-Class I

HLA-Class II

A

B

C

A

B

A

B

C

D

E

F

G

H

PEGYLATED FIBRINOGEN-BASED BIOMATRIX

CROSS REFERENCE TO RELATED APPLICATIONS

This application is a continuation-in-part and claims priority under 35 U.S.C. §120 of PCT Application No. PCT/US03/13697, filed May 1, 2003, which claims the benefit of priority under 35 U.S.C. §119(e) of U.S. Application No. 60/337,148, filed May 2, 2002 and Ser. No. 60/382,985, filed May 24, 2002.

TECHNICAL FIELD

The invention involves methods and materials related to fibrin-based biomatrices.

BACKGROUND

Heart failure is an increasingly common clinical problem that affects 8 of every 100 individuals past the age of 70 years. Mechanical overload resulting from regional loss of functioning myocardium secondary to infarct can result in asymptomatic left ventricular dysfunction of long duration. During this time myocyte hypertrophy is commonly seen, but contractile function of isolated myocytes may remain normal despite abnormal chamber function. Prolonged overload, however, often leads to the development of overt congestive heart failure and the appearance of contractile dysfunction of isolated myocytes. Evidence for apoptosis in these failing hearts has been reported. In a general sense, the molecular and cellular basis for the syndrome of progressive heart failure results from the inability of damaged and apoptotic myocytes to be replaced, since cardiac myocytes are generally thought to be terminally differentiated.

Stem cells are cells that have extensive proliferation potential that differentiate into several cell lineages, and that can repopulate tissues upon transplantation. The quintessential stem cell is the embryonal stem (ES) cell, as it has unlimited self-renewal and multipotent differentiation potential. ES cells are derived from the inner cell mass of the blastocyst, or can be derived from primordial germ cells from a post-implantation embryo (embryonal germ cells or EG cells). ES and EG cells have been derived from mouse, and more recently from non-human primates and humans. When introduced into a blastocyst of an animal, ES cells can contribute to all tissues of that animal.

SUMMARY

The invention is based on the discovery that stem cells or progenitor cells can be delivered to a diseased heart using a fibrin-based biomatrix to assist or restore heart function. Fibrin-based biomatrices retain the advantages of tissue-equivalent fabrication normally associated with collagen-based biomatrices, yet exhibit the added advantage of not suppressing ECM synthesis. Fibrin forms a fibrillar network that can be compacted and potentially aligned by entrapped tissue cells, such as stem or progenitor cells, forming a tissue-equivalent similar to the fibrillar collagens.

In one aspect, the invention provides a method for repairing damaged tissue in a mammal by introducing, on or into a tissue in need of repair, a fibrinogen solution having stem or progenitor cells under conditions such that a fibrin biomatrix including the cells forms at or near the site of introduction. In one embodiment, the fibrinogen solution is PEGylated. Representative tissues include skin and cardiac tissue. The stem or progenitor cells can be bone marrow cells, and can be autologous to the mammal being treated. The conditions for forming the fibrin biomatrix can include introducing a solution having a fibrinogen-converting agent (e.g., a serine protease such as thrombin) to the fibrinogen solution. Either or both the fibrinogen and the thrombin in the respective solutions can be autologous to the mammal.

In another aspect, the invention provides a method of assisting tissue function in a mammal in need thereof including introducing, on or into a tissue, a fibrinogen solution having stem or progenitor cells under conditions such that a fibrin biomatrix including the cells forms at or near the site of introduction, and wherein the cells assist the tissue function of the mammal. Conditions for forming a biomatrix can include introducing a fibrinogen-converting agent (e.g., thrombin) to the fibrinogen solution and cells, either before of after the fibrinogen solution and cells have been introduced into the mammal. In one embodiment, the fibrinogen solution is PEGylated.

The invention also provides a method of delivering stem or progenitor cells to a tissue of a mammal by injecting, onto or in the vicinity of a surface of the tissue of the mammal, a fibrinogen solution including the cells. A fibrinogen-converting agent (e.g., thrombin) can be added to the fibrinogen solution with cells before or after the fibrinogen solution and cells are injected into the mammal. In one embodiment, the fibrinogen solution is PEGylated.

In yet another aspect, the invention provides a method for inducing stem or progenitor cells to differentiate including (1) providing the cells in a fibrinogen solution, and (2) introducing the fibrinogen solution onto a tissue of a mammal under conditions such that a fibrin biomatrix including the cells forms at or near the site of introduction and the cells differentiate. Conditions for forming a biomatrix can include introducing a fibrinogen-converting agent (e.g., thrombin) to the fibrinogen solution and cells before or after the fibrinogen solution and cells are introduced onto a tissue of the mammal. In one embodiment, the fibrinogen solution is PEGylated.

In another aspect, the invention provides a method for repairing damaged tissue in a mammal by introducing, on or into a tissue in need of repair, a thrombin solution having stem or progenitor cells under conditions such that a biomatrix including the cells forms at or near the site of introduction. Representative tissues include skin and cardiac tissue. The stem or progenitor cells can be bone marrow cells, and can be autologous to the mammal being treated. The conditions for forming the biomatrix can include introducing a fibrinogen solution to the thrombin solution before or after the thrombin solution and cells have been introduced into the mammal. Either or both the fibrinogen and the thrombin in the respective solutions can be autologous to the mammal. In one embodiment, the fibrinogen solution is PEGylated.

In another aspect, the invention provides a method of assisting tissue function in a mammal in need thereof including introducing, on or into a tissue, a thrombin solution having stem or progenitor cells under conditions such that a biomatrix including the cells forms at or near the site of introduction, and wherein the cells assist the tissue function of the mammal. Conditions for forming a biomatrix can include introducing a fibrinogen solution to the thrombin solution and cells, either before of after the thrombin solution and cells have been introduced into the mammal. In one embodiment, the fibrinogen solution is PEGylated.

The invention also provides a method of delivering stem or progenitor cells to a tissue of a mammal by injecting, onto or in the vicinity of a surface of the tissue of the mammal, a thrombin solution including the cells. A fibrinogen solution can be added to the thrombin solution with cells before or after the thrombin solution and cells are injected into the mammal. In one embodiment, the fibrinogen solution is PEGylated.

In yet another aspect, the invention provides a method for inducing stem or progenitor cells to differentiate including (1) providing the cells in a thrombin solution, and (2) introducing the thrombin solution onto a tissue of a mammal under conditions such that a biomatrix including the cells forms at or near the site of introduction and the cells differentiate. Conditions for forming a biomatrix can include introducing a fibrinogen solution to the thrombin solution and cells before or after the thrombin solution and cells are introduced onto a tissue of the mammal. In one embodiment, the fibrinogen solution is PEGylated.

In addition to or in place of the stem or progenitor cells, a therapeutic compound (e.g., a drug) can be used in the biomatrix.

In another aspect, the invention provides an article of manufacture, comprising a fibrinogen solution; a thrombin solution; and instructions for forming a fibrin biomatrix. An article of manufacture can further comprise instructions for collecting stem or progenitor cells from a mammal, and/or a therapeutic compound such as a drug. In one embodiment, the fibrinogen solution is PEGylated.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 2A shows the differentiation of MSCs into chondroblasts based on toluidine blue and type II collagen staining. FIG. 2B shows the detection of alkaline phosphatase following osteogenic differentiation from sMSCs, while FIG. 2C shows the detection of calcium following osteogenic differentiation from sMSCs.

FIG. 3A shows the maximum expression of β-galactosidase was achieved at 1500 to 2000 MOI, while FIG. 3B shows transduced sMSC stained with β-gal to determine the transduction efficiency.

FIG. 5A shows a patch applied to the LV anterior wall of the proximal segment of the first diagonal branch of the left anterior descending coronary artery (LAD). FIG. 5B shows MRI multislice cine images of a heart with sMSC transplantation; arrows point to the fibrin-MSC patch. FIG. 5C shows that in sMSC-transplanted LV, X-Gal staining was observed in the infarct area. FIG. 5D shows the migration of transduced sMSCs ("blue cells) in culture from specimens taken from the peri-scar area. FIG. 5E shows the continued division of transduced sMSC cells maintained in stem cell culture medium. FIGS. 5F, 5G, and 5H show that the transduced sMSC cells were surviving and differentiating in the myocardial infarct region based on light microscopy. FIG. 5I shows a pathologic section of the specimen that includes the interface between the fibrin patch (shown in pale white) and the injured myocardium (shown in red). FIG. 5J shows a new vessel growing into the patch. FIG. 5K shows the immunohistochemistry staining of the interface between the patch and periscar, and shows a rich neovascularization in the scaffold of patch area. FIG. 5L shows the PCR amplification products from transduced sMSC cells, which demonstrates that Ad5RSVLacZ nucleic acid is present in the "blue cells."

Like reference symbols in the various drawings indicate like elements.

DETAILED DESCRIPTION

Figure 1:
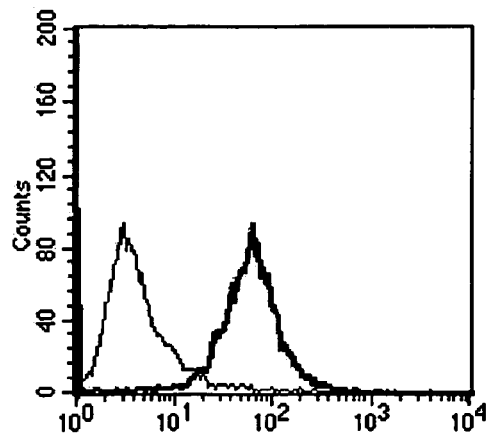
FIG. 1 shows the presence or absence of surface antigens on sMSC based on flow cytometry (thick line). The thin line profiles represent mIgG-staining isotype as a control.
Figure 1:
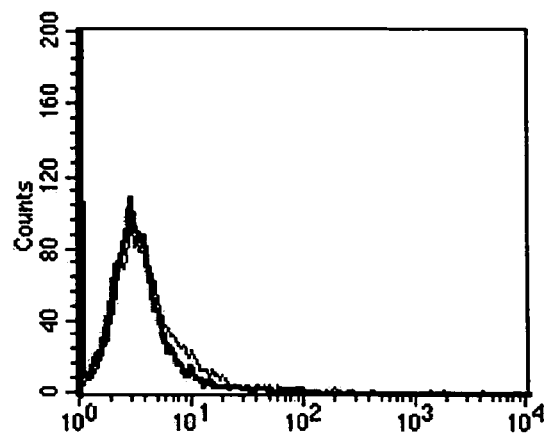
Figure 1:
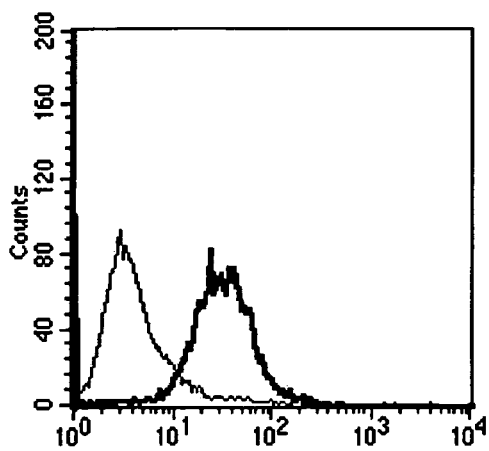
Figure 1:
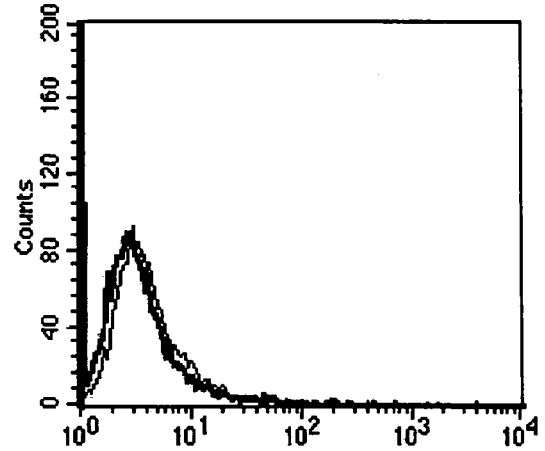

The invention provides methods and materials related to the administration of stem or progenitor cells to a mammal having damaged tissue. (e.g., congestive heart failure, left ventricular dysfunction, myocardial infarction, cirrhosis, bone fracture, or dermal abrasions). Administering stem or progenitor cells to such a mammal using the biomatrices described herein provides assistance to and improvement in tissue function in that mammal. The biomatrices of the invention can deliver a high concentration of stem or progenitor cells onto a tissue. In addition to the stem or progenitor cells, or alternatively to the stem or progenitor cells, the biomatrices of the invention can deliver a therapeutic compound such as a drug. In some cases, a high concentration of autologous bone marrow mononuclear cells can be administered to a mammal within 30 minutes following arrival at a patient care facility, greatly improving that mammal's chance of survival and response to therapy. In addition, the biomatrices described herein allow cells to leave the biomatrix and home to damaged tissue and facilitate repairs. Further, in vitro formation of a biomatrix of the invention allows the included cells to partially differentiate and develop function before implantation.

Biomatrices

The invention provides a biomatrix capable of providing support to biomatrix components, such as cells. Typically, a biomatrix can be formed from a fibrinogen solution (i.e., a solution containing fibrinogen polypeptides) by combining the fibrinogen solution with a solution containing a fibrinogen-converting agent. Such agents include without limitation, proteases such as serine proteases (e.g., thrombin). Other fibrinogen-converting agents suitable for converting fibrinogen to fibrin include, without limitation, mutant forms of thrombin exhibiting increased or decreased enzymatic activity. Without being bound by a particular mechanism, fibrinogen in the fibrinogen solution is converted to fibrin through a proteolytic reaction catalyzed by a serine protease in the serine protease solution. Fibrin monomers then aggregate to form a flexible biomatrix.

Fibrin biomatrices can be made such that an additional component is incorporated into the forming biomatrix. For example, mesenchymal stem cells (MSCs) can be added to the biomatrix, either to a fibrinogen solution or to a thrombin solution such that, upon addition of a thrombin solution to the fibrinogen solution or addition of a fibrinogen solution to a thrombin solution, the biomatrix that is formed includes the MSCs. In addition to stem or progenitor cells, a therapeutic compound can be incorporated. As used herein, a therapeutic compound includes without limitation a sense or an antisense oligonucleotide; a polypeptide or protein such as an antigen, a cytokine, or a fragment thereof; a carbohydrate; a chemical or a mixture of chemicals; an extract isolated from bacterial, plant, fungal or animal matter; an antibody; or a drug such as an antibiotic.

Fibrinogen solutions that contain about 50 mg/mL to about 400 mg/mL fibrinogen and thrombin solutions containing about 250 IU/mL to about 2000 IU/mL thrombin are suitable for making biomatrices. Typically, a fibrinogen solution containing about 120 mg/mL fibrinogen and a thrombin solution containing about 500 IU/mL thrombin are used to make a fibrin-based biomatrix compatible with cell survival and function. Flexibility can be altered by adding fibrinolytic inhibitors (e.g., tranexamic acid at 9.2% w/v, or aprotinin at 3000 KIU/ml, where KIU is kallikrein IU) or anticoagulants (e.g., trisodium citrate at 3-10 mg/ml, or glycine at 10-40 mg/ml) to either or both the solutions. In addition, such components can be used to alter the polymerization time associated with biomatrix formation. Typically, a biomatrix of the invention reaches a gel-like state within a few seconds of solution mixing, and stabilizes into a flexible semi-solid state within 1 minute. These times can be altered using the components listed above, or additionally by varying the concentration of fibrinogen, fibrinogen-converting agent, or cofactors that assist in fibrinogen conversion (e.g., $CaCl_2$).

Biomatrix components, such as fibrinogen and thrombin, can be obtained commercially from, for example, Sigma (St. Louis, Mo.). Alternatively, autologous fibrinogen or thrombin can be isolated from a mammal and used for biomatrix formation.

Other materials suitable for making a biomatrix include, without limitation, purified type I, II, or IV collagens; cell-contracted collagen including other components of the extracellular matrix such as proteoglycans or glycosaminoglycans, glycoproteins (e.g., fibronectin and laminin), elastin and/or bioactive peptide growth factors or cytokines; synthetic biodegradable fibers made from polymers such as polylactic or polyglycolic acids, polycaprolactones, or polyamino acids, or their copolymers; and composite structures such as collagen/polylactic acid structures.

PEG is a nontoxic and amphophilic compound, i.e. soluble both in water and in most organic solvents. Protein PEGylation is generally achieved via stable covalent bonds between an amino or sulfhydryl group on a protein and a chemically reactive group (carbonate, ester, aldehyde, or tresylate) on the PEG The resulting structures can be linear or branched. The reaction can be controlled via factors such as protein type and concentration, reaction time, temperature, and pH value. Environmental factors such as these likewise influence electrostatic binding properties and protein charge, form, and size.

PEGylation generally improves molecular properties. PEGylation typically improves the stability, biological half-life, water solubility, and/or immunologic characteristics of a protein. As a protein is more or less surrounded by the attached PEGs, PEGylated proteins are less rapidly broken down in the body than are unmodified proteins. PEGylation also reduces the rapidity and intensity of an immune system reaction against the protein. See, for example, U.S. Pat. Nos. 6,420,339 and 6,552,170.

Cell Types

Various types of cells can be included in a biomatrix. Cells having an established function can be included in a biomatrix to facilitate repairs or improve the function of a particular tissue (e.g., heart, lung, skin, bone, liver, kidney, pancreas, testis, and ovary). For example, a fibrin-based biomatrix for improving pancreas function in a mammal can include pancreatic beta cells. Other cell types suitable for particular tissue types and applications include, without limitation, islet cells, epithelial cells, endothelial cells, hepatocytes, nephrocytes, glomerulocytes, osteocytes (e.g., osteoblasts and osteoclasts), lymphocytes (e.g., T cells, B cells, and NK cells), granulocytes (e.g., neutrophils, basophils, eosinophils, and mast cells), and fibroblasts. In addition, cell types that have been engineered to perform a particular function, such as genetically altered cells, also can be included in a biomatrix. For example, a fibrin-based biomatrix can include cells that have been transfected with a transgene.

Cells having the ability to differentiate into various cell types also can be included in a biomatrix. Such cells include, without limitation, stem cells and progenitor cells. Stem cells are cells with extensive proliferation potential that can differentiate into several cell lineages. For example, embryonal stem (ES) cells have unlimited self-renewal and multipotent differentiation potential. Stem cells have been identified in many tissues. Typical stem cells include, without limitation, hematopoietic, neural, gastrointestinal, epidermal, hepatic, mesenchymal stem cells (MSCs), stem cells from exfoliated deciduous teeth, and autologous bone marrow stem cells (ABMSCs). Progenitor cells have multipotent differentiation and extensive proliferation potential. Progenitor cells can differentiate in vitro into most mesodermal cell types including cells with characteristics of skeletal and cardiac myoblasts, as well as cells with endothelial and smooth muscle features. Any combination of cells can be included in a biomatrix of the invention.

Stem or progenitor cells can be obtained from various species including, without limitation, mouse, rat, dog, pig, cow, goat, horse, non-human primates, and humans. Although allogeneic and xenogeneic cells are within the scope of the invention, autologous stem or progenitor cells are typically used. Stem or progenitor cells can be isolated from various tissues including, without limitation, brain, spinal cord, lung, skin, liver, blood, and bone marrow. The use of autologous bone marrow mononuclear cells allows a mammal in need of cell therapy to receive those cells within a short time (e.g., 30 minutes). For example, stem cells can be isolated from bone marrow aspirated from a mammal. Briefly, a needle is used to penetrate the outer core of a bone (e.g., the iliac crest) in an anesthetized mammal. When using a syringe, negative pressure is applied by forcefully withdrawing the syringe plunger, allowing the marrow to be collected in the syringe barrel. The marrow is then layered onto a gradient substrate (e.g., Ficoll) in a conical tube. The marrow is then centrifuged to collect autologous bone marrow mononuclear cells at a known interface. After subsequent culture selection, the ABMSCs can be manipulated (e.g., transfected with a plasmid or transduced with a virus) prior to use. Alternatively, techniques such as those disclosed in U.S. Pat. 5,486,359 and 6,261,549 also can be used for isolating, purifying, and characterizing stem and progenitor cells suitable for the invention.

Administering Cells to a Mammal

Cells, such as those described herein, can be administered to a mammal in various ways. Although cells can be administered to a mammal as a cell suspension without any additional components, the methods of the invention typically involve administering cells in a biocompatible medium, which is, or becomes in situ at a desired site, a semi-solid or solid biomatrix. For example, a fibrin-based biomatrix can be formed in vitro in the presence of ABMSCs to yield a flexible, solid biomatrix including the ABMSCs. As described above, methods for forming such a biomatrix involve including cells in either a fibrinogen solution or a fibrinogen-converting agent solution so that, upon mixing the two solutions under conditions that promote matrix formation, the cells are distributed throughout the forming biomatrix. Once the biomatrix is formed, it can be transplanted into a mammal in need thereof using any technique suitable to the particular circumstance. Alternatively, biomatrix components can be delivered to a site such that a biomatrix including cells is formed at the site in vivo. Such sites can be external or internal to a mammal. For example, a fibrinogen solution containing ABMSCs and a thrombin solution can be introduced topically to a dermal abrasion, whereupon a fibrin-based biomatrix including the ABMSCs forms on the surface of the abrasion. In another example, a fibrinogen solution containing ABMSCs and a thrombin solution can be introduced onto the surface of the myocardium, whereupon a fibrin-based biomatrix including the ABMSCs forms.

Various methods can be used to deliver biomatrix components to a site such that a biomatrix including cells is formed at the site in vivo, provided that the components and cells can perform their intended functions. Such methods include, without limitation, aerosol- or spray-based deposition, expandable biocompatible foam-based deposition, and injection. In one embodiment, a fibrinogen solution containing ABMSCs is loaded into a first syringe, and a thrombin solution is loaded into a second syringe. The loaded syringes are connected (e.g., using a Y-shaped connector) such that the two solutions, when expelled from the syringes, mix prior to their deposition on a myocardium. The deposited mixed solutions form, on the myocardium, a flexible, solid biomatrix containing ABMSCs. The presence of the biomatrix enhances the opportunity for the administered ABMSCs to proliferate, differentiate, and functionally integrate into the myocardium.

Articles of Manufacture

The invention further provides for articles of manufacture to generate a biomatrix of the invention. An article of manufacture according to the present invention can include a fibrinogen solution and a thrombin solution, together with suitable packaging materials. Suitable fibrinogen and thrombin solutions, as well as appropriate concentrations of fibrinogen and thrombin within each solution, are described above.

Articles of manufacture of the invention also can contain a package insert or package label having instructions thereon for using the solutions to form a biomatrix. Articles of manufacture may additionally include a package insert or package label having instructions thereon for collecting stem or progenitor cells from a mammal. Articles of manufacture of the invention can further include a therapeutic compound such as a drug, and can additionally include reagents for forming a biomatrix and/or for carrying out the methods disclosed herein.

The invention will be further described in the following examples, which do not limit the scope of the invention described in the claims.

EXAMPLES

Example 1

General Methods and Materials

Animals: Pigs (e.g., 30-40) can be used for testing various biomatrix compositions. Surgical procedures are performed using appropriate anesthetic agents. No muscle relaxants are used. Analgesia is maintained with butorphanol, 0.2-0.4 mg/kg subcutaneously 4 h during the first 24 hours after the instrumentation surgery and then as needed for relief of discomfort. Intake of food is monitored and intravenous fluids are administered in animals that fail to drink adequately or have evidence of dehydration as demonstrated by decreased turgor. Euthanasia is performed by intravenous administration of an euthanasia solution (e.g., an overdose of sodium pentobarbital 200 mg/kg iv and 25 mg/kg sodium phenytoin iv) to induce cardiac arrest. This method is consistent with the recommendations of the Panel of Euthanasia of the American Veterinary Medical Association.

Experimental groups: The number of animals for each group was calculated according to Rosner's equation (see, Rosner, B., *Fundamentals of Biostatistics*, chapter 10, p. 322-323, 1986) using values for power=0.80 and significance level=0.05. The left ventricle (LV) ejection fraction or myocardial CP/ATP ratios from previous studies of this animal model were used for this calculation. See, Zhang, J., et al., *Circulation*, 94:1089-1100, 1996; Murakami, Y. et al, *Circulation*, 99:942-948, 1999; Murakami, Y., et al., *Am. J. Physiol.*, 276:H892-H900, 1999. According to this calculation, 6 pigs in sham-operation group, and 16 pigs in each of patch transplantation group can be used to examine each hypothesis. The three groups are as follows: Group 1, sham-operated normals; Group 2, left anterior descending coronary artery (LAD) ligation with placebo biomatrix (i.e., no cells) transplantation; Group 3, fibrin biomatrix with stem cells transplantation. The 3 groups undergo the identical protocols to examine the respective hypothesis. Each protocol uses 38 animals, for a total of 114 animals. In considering the acute (24-36 hour) postinfarction death rate (~15%), a total of 134 animals are needed. Statistical analyses are performed as studies are carried out, so that protocols can be terminated as soon as a statistically significant result has been achieved.

Non-invasive $^{31}$P-MRS imaging with external coil: MRI studies were conducted on a 4.7 Tesla/40 cm SISCO system using $^{31}$P-MRS with an external coil to examine myocardial phosphates non-invasively. In these noninvasive studies, the transmural distribution of $^{31}$P metabolites from cylindrical regions across the LV wall of a closed-chest model was measured.

Spatially localized $^{31}$P NMR spectroscopy in open chest animals: Spatially localized $^{31}$P NMR spectroscopy is performed in open chest animals using the RAPP-ISIS method. CP, ATP, and Pi levels corresponding to the integrals of each resonance peak are serially monitored throughout the study. The chemical shift of Pi relative to that of CP is used to calculate cytosolic pH.

Image analysis of the MRI cine studies: Imaging data are evaluated using an automatic segmentation program. Ventricular volumes, ejection-fraction, LV diastolic and systolic volumes, absolute myocardial mass from multi-slice, multi-phase MR cine images are automatically calculated. The left ventricular end-diastolic volume (Vd) and end-systolic volume (Vs) of each slice is represented by the area enclosed by the endocardium.

Tissue Preparation: At the end of the study, immediately after the last spectrum is acquired, biopsies are obtained. These biopsies are stored at −80° C. for subsequent biochemical measurement of concentrations of ATP and total creatine.

Immunohistochemistry: Immunohistochemistry is utilized for detection of mesenchymal stem cells transplanted into the pig myocardium. 5-8 mm thick frozen sections mounted on positively-charged slides are dried and fixed with 4% acetone for 10 minutes and air dried for 60 minutes. Endogenous peroxidase activity is removed by incubation with 3% $H_2O_2$ and methanol for 10 minutes. After blocking non-specific protein binding with 5% normal goat serum, slides are incubated overnight at 4° C. with polyclonal goat IgG against Troponin I, serving as primary antibody, diluted in PBS/Tween20+1% NGS. Pig ABMSCs are transduced with a retrovirus so that they express β-galactosidase, so that after transplantation they can be detected by staining for β-galactosidase activity.

Detection of ABMSC differentiation into vessels: Whether transplanted ABMSCs differentiate into vessels containing endothelial cells and smooth muscle cells can be examined. The engrafted area is examined using high power magnification with H&E staining to look for vessels. The appearance of GFP or β-galactosidase in the cells forming the new vessels indicates that the vessels were formed from the grafted stem cells. The differentiation of stem cells into endothelial cells in the vessels is monitored by immunohistochemistry or immunofluorescence using antibodies against von Willebrand factor, Fltl, Tie, Tek, PECAM, and P and E-selectins. Antibodies against smooth muscle myosin heavy chain, smooth muscle α-actin, and desmin are used to monitor differentiation to smooth muscle. Immunostaining using an antibody against connexin 43 (the connexin most highly expressed in endothelial cells, and also expressed in smooth muscle cells) is used to monitor contact sites between endothelial cells and other cells, including smooth muscle. Imaging is performed using confocal microscopy.

Electron Microscopy: Electron microscopy is employed to examine the ultrastructural properties of the grafted stem cells and their interaction with host cells. Preparation of the tissue for transmission electron microscopy is performed as described by Watanabe et al. (*Cell Transplantation*, 7:239-246, 1998). Briefly, tissue blocks are fixed in glutaraldehyde in sodium cacodylate buffer and postfixed in 1% osmium tetroxide in sodium cacodylate. Tissue is then stained in 0.5% uranyl acetate, dehydrated through a graded alcohol series and embedded in Polybed 812 (Polysciences Inc., Warrington Pa.). Grafts are located by staining 1 mm sections with toluidine blue. The block is thin-sectioned and poststained with lead citrate. Specimens are examined in a transmission electron microscope.

Experimental preparation for final open chest MRS study: Animals are anesthetized with α-chloralose (100 mg/kg and 20 mg/kg/hr iv) following sedation with ketamine (20 mg/kg im).

Measurements for open-chest MRS studies: The following measurements can be obtained during each experimental condition unless otherwise stated: transmural differentiated $^{31}P$-MRS determination of HEP and Pi levels; systolic thickening fraction of areas with cell transplantation and remote region; myocardial blood flow; aortic and left ventricular pressures; $MVO_2$.

Experimental interventions for Open-chest MRS studies: After all the baseline data are obtained, pigs receive adenosine (1 mg/kg/min iv) to achieve maximum coronary vasodilation and all measurements are repeated. This intervention is to examine myocardial blood flow reserve. The adenosine infusion is then discontinued and recontrol data are obtained in the following 10 minutes. To examine the contractile reserve, dobutamine stimulation (20 µg/kg/min iv) is then started. After waiting for ~10 minutes to allow the systemic hemodynamics to become stable, all measurements are repeated.

Example 2

A Fibrin-Based Biomatrix for Delivering Stem Cells to Ischemic Myocardium

In response to myocardial ischemic signals, it is hypothesized that the stem cells leave the fibrin patch and home to ischemic myocardium to repair the infarct region. A fibrin biomatrix delivers a relatively high number of stem cells onto the surface of the myocardial infarct, thereby providing optimal conditions for the cells to respond to the ischemic stimuli and to home into the damaged region and to differentiate. Such a biomatrix can be delivered by a minimally invasive method.

Methods for fibrin patch entrapping ABMSCs: Lyophilized human fibrinogen is reconstituted by adding 5 ml of buffer solution (150 mM of sodium chloride, 0.02% of polysorbate 80, and 0.003% trypsin inhibitor and 2% glycine, pH 6.9-7.4). Likewise, lyophilized thrombin is reconstituted by adding 5 ml of 200 µmole of $CaCl_2$ to a vial containing 2500 IU of thrombin, resulting in an activity of 500 IU/ml of thrombin solution. Stem cell suspensions are then prepared. Cells transfected with a recombinant LacZ gene are harvested from cultures using 0.05% trypsin/0.6 mM-EDTA (Gibco) and washed with PBS and saline in succession. $5\times10^6$ cells are resuspended in 5 ml of reconstituted thrombin solution before the application. Equal volumes (5 ml) of the reconstituted fibrinogen solution and thrombin solution containing $5\times10^6$ ABMSCs are drawn into separate 5 ml syringes respectively, which are then attached to a Y-shaped plastic connector. A single 24 gauge intravenous needle is attached to the Y-connector, in which good mixing of constituents from the two syringes occurs and is used to apply the mixture by pushing the two syringe plungers simultaneously.

Yorkshire swine (45 days of age; ~10 kg) are anesthetized with intravenous sodium pentobarbital (20 mg/kg, iv). A left thoracotomy is performed. Approximately 0.5 cm of the LAD distal to the first diagonal vessel is dissected free. The LAD is occluded by a ligature for 120 minutes. The ligature is then removed. Following LAD reperfusion, the animals are observed in the open chest state for 30 minutes. If ventricular fibrillation occurs, immediate electrical defibrillation is usually successful. To apply the fibrin biomatrix, a slight scratching on the epicardial surface of the anterior wall is produced with a scalpel blade, which is necessary to allow bonding of the biological adhesives of the fibrin gel. Once the scratching is completed, 5-10 ml of fibrinogen solution mixed with 5 mL of thrombin solution containing ABMSCs or placebo (i.e., no cells) is applied to the scratched area. The chest is then closed in layers. If the heart is dilated as a result of the infarct, the pericardium is left open. Animals are examined using MRI/MRS once every two weeks, and undergo a final study 6 weeks after infarct. Six weeks after the operation, the animals are anesthetized, and the incision reopened. The patch-applied area is examined for adhesion, fibrosis and remnants of the fibrin matrix. The heart is excised and the integrated specimens including fibrin patches and myocardium are resected and frozen in liquid nitrogen or fixed in 4% paraformaldehyde for blot, PCR, histological and immunohistochemical analyses.

These studies can clarify: 1) whether the transplanted ABMSCs delivered by a fibrin patch proliferate and differentiate in the infarct region, and 2) whether ABMSCs form contacts with host myocytes. The transplanted cells are characterized using X-gal staining. It is hypothesized that following the patch transplantation, the ABMSCs migrate into the ischemic region and divide and differentiate to form a new contractile mass. LV function and myocardial energetics are examined by MRI/MR spectroscopy (MRS) after 2 weeks. Final open chest MRS studies are performed 6 weeks after cell transplantation. Morphologic studies examine whether the cardiac gap junction protein, connexin 43, is present at the interface between transplanted "blue" cells and host myocytes.

Example 3

A Fibrin-based Biomatrix for Delivering ABMSCs to Infarcted Myocardium

It is hypothesized that ABMSCs embedded within a fibrin biomatrix gradually leave the biomatrix and migrate to the infarct area where they continue to divide and differentiate into myocytes, smooth muscle cells, and endothelial cells, and replace the infarcted myocardium.

This protocol is based on the concept that, in nature, myocardial ischemia may be able to cause ABMSC selection, expansion, and differentiation. Bone marrow stem cells can be transfected with the reporter gene β-galactosidase. The application is completed by a minimal invasive method without open chest surgery.

Sixteen normal juvenile pigs (45 days of age, ~10 kg) in each of the 3 groups (Group 1, sham-operated controls; Group 2, LAD ligation with placebo (i.e., no cells) transplantation; Group 3, bone marrow stem cell patch transplantation), undergo the identical protocol as follows:

Bone marrow stem cell collection (Iliac Crest Aspiration): General anesthetic is given (pentobarbital 30 mg/kg/iv with supplemental doses as required for comfort and immobilization). The animal is restrained in an appropriate position to access the site of aspiration. An aspiration needle is used to penetrate the outer cortex of bone. After bone penetration, the stylet is removed. A 20 ml syringe is then attached to the aspiration needle and negative pressure is applied by forcefully withdrawing the syringe plunger. Bone marrow (dark red, more viscous than blood, and containing fat particles) is drawn up into the syringe in response to the applied negative pressure. The collected marrow sample is layered onto Ficoll-Paque—1077 (Sigma) in a 50 ml conical tube. The sample is then centrifuged at 400 xg for 30 minutes at room temperature. The mononuclear cells are collected from upper layer and interface, diluted with 2-3 volumes of Dubecco's PBS and collected by centrifugation at 1000 rpm. The collected cells are resuspended and seeded at a density of 200,000 cells/cm$^2$ in T-75 flask coated with 10 ng/ml fibronectin (FN). The seeded cells are cultured in medium consisting of 60% low-glucose DMEM (Gibco BRL), 40% MCDB-201 (Sigma), 1× insulin transferrin selenium, 1× linoleic acid bovine serum albumin (LA-BSA), 0.05 nM dexamethasone (Sigma), 0.1 mM ascorbic acid 2-phosphate, 2% FCS, penicillin and streptomycin (100 U/ml). After 3 days, non-adherent cells are removed by replacing the medium. The attached cells develop colonies and continue dividing. About 5-7 days, the primary cultures of ABMSCs reach nearly 90% confluency. ABMSCs are subcultured by incubation with trypsin. The first passage cells are plated at 4000-5000 cells/cm$^2$ and are further cultured two days prior to transduction with AdRs-vLacZ. After overnight incubation with recombinant viruses in serum-free DMEM, the ABMSCs are washed with medium and collected, then washed several times with saline. The washed ABMSCs are resuspended in 0.5 ml of saline prior to transplantation.

Transplantation of the fibrin-based biomatrix containing ABMSCs: Yorkshire swine (45 days of age; ~10 kg) are anesthetized with intravenous sodium pentobarbital (20 mg/kg, iv). A left thoracotomy is performed. Approximately 0.5 cm of the LAD distal to the first diagonal vessel is dissected free. The LAD is occluded with a ligature for 120 minutes. The ligature is then removed. Following LAD reperfusion, the animals are observed in the open chest state for 30 minutes. If ventricular fibrillation occurs, immediate electrical defibrillation is usually successful. The fibrin-based biomatrix containing the bone marrow stem cells is then applied as described in Example 2. The chest is then closed in layers. If the heart is dilated as a result of the infarct, the pericardium is left open. Animals are examined using MRI/MRS once every two weeks, and undergo a final study 6 weeks after infarct. For the final open chest study, instrumentation is performed for systemic homodynamic and LV wall thickening measurements as described in the methods section.

Data Interpretation: Since adult cardiomyocytes are terminally differentiated, they cannot regenerate so that large acute myocardial infarction in swine leads to aneurysm formation, often with congestive heart failure. Adult stem cells are transplanted using a fibrin-based biomatrix patch to attempt to prevent this progression onto LV infarct. MRI/MRS is used to monitor cardiac function and myocardial energy metabolism in vivo for eight weeks. Should islands of blue cells (X-gal) exhibit the characteristics of cardiac myocytes, and on double staining show Troponin I positivity in ABMSC transplanted areas, it will indicate not only that the transplanted cells survive, but also differentiate into myocytes, supporting the concept that stimuli exist in the damaged organ that will promote the ABMSCs to differentiate into the locally appropriate cell lineages. In pigs in which cells are transplanted, if systolic wall thickening is improved and the cardiac gap junction protein, connexin 43 is identified at the interface between implanted cells and host cardiomyocytes, demonstrate that ABMSCs may regenerate into functioning muscle that assists LV contractile performance. If new vessels are formed from ABMSCs, it will further support that ABMSC transplantation is a useful therapeutic modality for myocardial infarct or postinfarction LV remodeling.

Contractile Performance: The main aim of this experiment is to examine whether ABMSC transplantation will improve the myocardial contractile performance. It is known that swine hearts without cell transplantation develop LV aneurysm in ~4 weeks following the LV infarction. If the ABMSC transfer prevents the LV aneurysm and improves the LV contractile performance, this beneficial effect can be identified by the MRI follow-up data, namely an increased LV ejection fraction and less thinning in the infarct areas. The LV thickening fraction data measured by epicardial crystal transducers placed on the infarction area in comparison to the remote area demonstrates whether the evolving ABMSC tissue can contract synchronously with the LV. The contractile reserve of the ABMSC engraft by measuring the percent increase of the thickening fraction in response to dobutamine stimulation will be examined, as well as the increase in LV dP/dt in comparison to hearts without cell transplantation. In order for the engraft to assist LV contraction at increasing cardiac workstates, vessels must grow into the graft. Microsphere data at baseline and during hyperaemia or catecholamine stimulation, will provide regional blood reserve evaluations.

Formation of new vessels from the transplanted ABMSCs: In order to maintain transplanted ABMSC viability, there must be new vessel growth into the grafted areas. The grafted area can be examined using high power magnification with H&E staining to look for new vessels. The appearance of GFP or β-galactosidase in the cells forming the new vessels indicates that the vessels are derived from the ABMSCs.

Electromechanical coupling of implanted cells: Cardiac cells are electrically coupled to adjacent cells via specialized gap junctions, composed of hexamers of the protein connexin, which allow the exchange of ions and small molecules between adjacent cells. If gap junctions with connexin 43 are found at the interfaces between transplanted "green" cells and host myocytes it supports the concept that mechanical and electrical coupling between transplanted cells and host myocytes can occur in hearts with cell transplantation. Electron microscopy is used to demonstrate the ultrastructural properties of the grafted ABMSC and their interaction with host cells. If gap junctions and adherin-type junctions are formed between the grafted and host cells, it supports the concept of electromechanical coupling between the grafted cells and host cells. If the connexins are found only in the in vivo experiment but not in the in vitro co-culture of ABMSCs and adult myocytes it supports the concept that the strongest stimuli for survival of the transplanted cells to form contacts, to differentiate to the different lineages, and to contract synchronously is provided by cues generated locally in the beating heart.

Myocardial energy metabolism: It is known that the myocardial energy charge is decreased in failing and hypertrophied hearts. This abnormality is directly related to the severity of the hypertrophy and is most severe in hearts with CHF. The hypothesis that these myocardial energetic changes contribute to the transition to heart failure is controversial. The data from the proposed studies may provide insight into understanding the relationships between the decreased myocardial energetic state and the transition to heart failure in hearts with postinfarction LV remodeling. If in response to cell transplantation, the LV function improves with accompanying improvement of myocardial energetics, it supports the concept that a decreased myocardial energetic state contributes to the decreased LV contractile function. If the LV function improves with no improvement of myocardial energetics, the data indicate that the abnormal myocardial energetics is not the cause of the LV dysfunction. It is known that the CP/ATP ratio is higher in fast twitch skeletal muscle than in fatigue resistant cardiac muscle. Spatially localized MRS is used to examine whether HEP metabolism changes to more closely resemble fatigue resistance cardiac muscle over the time when ABMSCs are differentiating into cardiomyocytes in the beating heart.

Example 4

A Tissue Equivalent Biomatrix Populated with Myocyte-like Cells

Bioartificial myocardium is generated by entrapping ABMSC-derived cardiomyocytes into a dilute fibrin biomatrix. Culture conditions are used such that the cells contract and align the fibrin network, and replace it with cell-derived extracellular matrix (ECM) that adopts the alignment of the degrading fibrin. Cell alignment is used to maximize cell-cell junctions and coordinated contraction. Samples fabricated under culture conditions that also match myocardial compliance and possess sufficient tensile strength are implanted onto the infarct region to reestablish LV contractile function. The cells are in a tissue-like environment before implantation, allowing direct application of chemical, electrical, and mechanical cues in vitro to guide cell differentiation and tissue remodeling. The resulting compacted network of fibrin matrix provides structural and mechanical support for the implanted cells, possibly promoting healing of the infarct. The studies can clarify: 1) whether the ABMSC-derived cardiomyocytes entrapped in reconstituted fibrin gel form a ABMSC-myocardial patch that has cellular, mechanical, and electromechanical characteristics comparable to native tissue, and 2) whether a ABMSC-myocardial fibrin patch implanted into an LV infarct shows greater benefits than stem cell patch transplantation.

Fabrication: Tubular forms of the ABMSC-myocardial fibrin patch are fabricated allowing uniaxial (circumferential) alignment of the cells and cell-produced ECM that is desired to facilitate coordinated contraction. The concentration of fibrinolysis inhibitor (ACA) needed is determined as well as the optimal concentrations of TGF-β and insulin in terms of ultimate mechanical and electromechanical properties. It is expected that the initial cell concentration can be optimized as well. Isotropic tubes are fabricated using adhesive mandrels (no agarose coating) to assess the benefits of alignment.

Biological Characterization: Cell viability and number is determined in situ. Viability is measured using a Molecular Probes Live/Dead Reduced Cytotoxicity kit (L-7013). Numbers are assessed by collagenase digestion of the gel followed by a Pico Green assay (Molecular Probes) to quantify DNA and estimate total cell number. Immunostaining using an antibody against connexin 43, the protein associated with gap junctions implicating contractile connectivity of the cardiomyocytes, with confocal imaging is performed to assess cell connectivity. Following incubation, cell and ECM alignment is characterized. Frozen sections are stained with a Hoechst assay and cell alignment determined from morphology. The collagen content is quantified by hydroxyproline assay, the proteoglycan content by an alcian blue stain assay, and the elastin content by hot alkaline extraction. Sections are also stained with Masson's trichrome stain and examined for spatial variations in collagen content, and similarly for proteoglycan content using safranin-o and for elastin content using indirect immunofluoresence. Other replicates are used to characterize the global structure and biomechanical properties. Global tissue structures are characterized using quantitative polarized light microscopy to generate an alignment map following fixation and longitudinal cutting to prepare a flat sample.

Mechanical Characterization: It is hypothesized that the ABMSC-myocardial fibrin patch provides a positive mechanical environment for the ABMSC-derived cardiomyocytes. To test this hypothesis, the mechanical properties of the ABMSC-gel composite is characterized and compared with the properties of myocardial tissue. The simplest test to perform is the uniaxial extension test, in which a sample is clamped on two sides and stretched. The force-displacement relationship provides a direct measure of the mechanical properties of the sample.

Electromechanical Characterization: The electromechanical response of the ABMSC-myocardial fibrin patch is also characterized in vitro.

Example 5

Functional Consequences of Biomatrices on LV Infarcts

Artificial tissue generated from ABMSCs is applied to a LV infarct after LAD occlusion using a biomatrix, and studies are carried out during the subsequent 4 and 8 weeks. It is expected that over 4 weeks the biomatrix is incorporated into the LV surface. Subgroups of animals are monitored for 4 and 8 weeks to examine if time-dependent improvement in function occurs. The functional consequences of autologous myocardial patching over the LV infarcts are examined by thickening fraction, dP/dt, tau, and the responsiveness to catecholamine stimulation. The ABMSC differentiation potential is examined by immunofluorescent staining as described in Examples 2-4. This study examines whether the myocardial patch using the artificial tissue from ABMSCs improves LV contractile performance and prevent the transition to heart failure.

Data interpretation: The main aim of this experiment is to examine whether the ABMSC-myocardial patch using ABMSCs develops contraction synchronous with the LV. It is known that hearts without myocardial patches develop LV aneurysm in 4 weeks following the LV infarction. If the myocardial patch prevents the LV aneurysm and improves the LV contractile performance, this beneficial effect is identified by the MRI follow-up data, namely the increased LV ejection fraction and less thinning in the infarct areas. The LV thickening fraction data measured by epicardial crystal transducers placed on the ABMSC-myocardial patch during the final open chest experiment demonstrates whether the artificial tissue generated from ABMSC contracts synchronously with the LV. The immunofluorescent double staining data are used to examine whether there are new vessels forming from the ABMSCs, or whether the new vessels are from angiogenesis from host cardiac cells. The contractile reserve of the ABMSC-myocardial patch is examined by measuring the percent increase of the thickening fraction in the patch area in response to dobutamine stimulation, as well as the increase in LV dP/dt in comparison to hearts without a myocardial patch. It is known that the CP/ATP ratio is higher in fast twitch skeletal muscle than fatigue resistant cardiac muscle. Spatially localized MRS is used to examine whether HEP metabolism changes to more closely resemble fatigue resistance cardiac muscle.

Example 6

Specific Materials and Methods

Studies were performed in accordance with the "Position of the American Heart Association on Research Animal Use", adopted Nov. 11, 1984, and protocols were approved by the Animal Care Committee of the University of Minnesota.

Adenovirus Vectors: Replication-deficient recombinant adenoviruses carrying the β-galactosidase reporter gene LacZ under the control of Rous sarcoma virus long terminal repeat (RSV-LTR) promoters were purchased from the University of Iowa Gene Vector Core (Dr. Richard Anderson). To test the vectors, swine mesenchymal stem cell (SMSC) were plated at a density of 5000 cells/cm$^2$ in 6 wells plates. Incremental concentrations of virus over the range of 100 to 15000 multiplicity of infection (MOI) were applied overnight in serum-free modified DMEM to determine the optimal transduction efficiency. The next day, the virus containing supernatant was removed, and the cells were washed several times with PBS and incubated in modified DMEM containing 2% FBS. Two days later, the cells were fixed in 1× fixation solution (2% formaldehyde and 2% glutaraldehyde in 1×PBS) for 10 minutes, and X-gal staining was performed (β-Gal Staining kit, Invitrogen). The β-galactosidase-positive (β-gal) blue cells were counted in 5 microscopic fields (20×) and expressed as a percent of the total number of cells in those fields.

Isolation of swine mesenchymal stem cells: sMSCs from bone marrow were isolated by gradient density centrifugation according to previous reports (Gronthos et al., 1994, *Blood* 84:4164-4173; Pittenger et al., 1999, *Science* 284:143-147). Briefly, bone marrow was aspirated from the sternum of healthy Yorkshire pigs into a syringe containing 6000 U heparin, and diluted with Dulbecco's PBS in a ratio of one to one. The marrow sample was carefully layered onto the Ficoll-Paque-1077 (Sigma) in a 50 ml conical tube and centrifuged at 400×g for 30 min at room temperature. The mononuclear cells were collected from the interface, washed with 2-3 volumes of Dulbecco's PBS and collected by centrifugation at 1000 rpm. The cells were resuspended and seeded at a density of 200,000 cells/cm$^2$ in T-75 flask coated with 10 ng/ml fibronectin (FN) and cultured in medium consisting of 60% low-glucose DMEM (Gibco BRL), 40% MCDB-201 (Sigma), 1× insulin transferin selenium, 1× linoleic acid bovine serum albumin (LA-BSA), 0.05 μM dexamethasone (Sigma), 0.1 mM ascorbic acid 2-phosphate, 2% FCS, 10 ng/ml PDGF, 10 ng/ml EGF, 100 U/ml penicillin and 100 U/ml streptomycin. After 3 days, nonadherent cells were removed by replacing the medium. The attached cells grew and developed colonies in 5-7 days. After approximately 10 days, the primary cultures of MSCs reached nearly 90% of confluence; cells were subcultured by incubation with trypsin. The first passage cells were plated at 4000-5000 cells/cm$^2$ and further cultured two days for transduction with AdRsvLacZ.

Cell Preparation for Transplantation: First passage sMSCs were plated at 5000/cm$^2$ in modified DMEM with 2% FBS. One day later, the cells were washed with serum-free modified DMEM and infected overnight with AdRSVlacZ at 1500 MOI. The supernatant was then removed, the cells washed with PBS, and then cultured with modified DMEM containing 2% FCS. The medium was repeatedly changed over 2 days (≧6 changes) to ensure complete removal of viral particles and to allow for the internalization of any particles remaining on the surface. On the day of surgery, the cells were harvested with 0.25% trypsin-EDTA (Invitrogen), washed with PBS, and resuspended in 0.5 ml saline.

Animal model: A swine model of postinfarction LV remodeling (Zhang et al., 1996, *Circulation* 94:1089-1099; Murakami et al., 1999, *Circulation* 99:942-948) was used to examine the behavior of autologous sMSCs homing to the heart. Briefly, young pigs (45 days) were anesthetized and a left thoracotomy was performed. The proximal segment of the first diagonal branch of left anterior descending coronary artery (LAD) was dissected free and occluded with a ligature. Defibrillation was applied when LV fibrillation occurred. After systemic hemodynamics had stabilized, the fibrin-sMSC patch was applied to the LV anterior wall. To apply the fibrin matrix, the epicardial surface of the anterior wall perfused by (LAD) was gently scarified with a scalpel blade, which is necessary to induce bonding of biological adhesives of the fibrin gel. After the surface was prepared, 5-10 ml of fibrin gel mixed with MSCs was applied to the scratched area. The thoracotomy was then repaired and the animal was allowed to recover. Sixteen days after surgery, the animals were returned to the laboratory for MRI and terminal studies.

Magnetic Resonance Imaging (MRI): All MRI studies were performed on a standard Siemens Medical System VISION® operating at 1.5 Tesla as previously described (Zhang et al., 1996, Circulation, 94:1089-1099).

Tissue Preparation: After the MRI experiments were completed, animals were anesthetized and the thoracotomy incision was reopened. The area of the patch was examined for adhesion, fibrosis and residual remnants of the fibrin matrix. The heart was excised and integrated specimens including the fibrin patch and the underlying myocardium were collected and either frozen in liquid nitrogen for blotting, PCR, and X-Gal staining, or fixed in 4% formaldehyde for histological and imunohistochemical analyses. The tissues were washed with cold PBS and then fixed with 2% formaldehyde and 0.2% glutaraldehyde in PBS for 1 to 2 hours (depending on the size of the tissue). The tissue was then washed in PBS for 5-10 min twice and incubated with X-gal staining solution (β-Gal Staining kit, Invitrogen) in a $CO_2$ incubator. The tissues were checked every half hour for blue staining. After 2.5 hours, the tissues were washed with PBS and immersed in 4% formaldehyde overnight. The tissues were dehydrated with increasing concentrations of ethanol and then embedded in paraffin. Sections 5-10 μm in thickness were cut and stained with Hematoxin & Eosin.

Histology and Microscopy to Evaluate Myocytes Differentiation: For immunohistochemistry staining to evaluate myocyte differentiation, the tissue sections were fixed for 10 minutes at room temperature with 4% paraformaldehyde solution and then washed with PBS twice. The sections were blocked with 5% BSA/0.3% triton-100 for 30 minutes and then incubated for 30 minutes with monoclonal primary antibody (Troponin T, Cardiac Isoform Ab-1, NeoMarkers), followed by Link solution incubation for 15 minutes and Streptavidin peroxidase incubation for 30 minutes, respectively (DAKO LSAB+Kit, peroxidase, DAKO Corporation). After thorough washing, chromogen substrate solution was applied for 5 minutes, and then the sections were counterstained with hematoxylin and finally mounted.

Analysis of β-galactosidase reporter gene in the patch and in the peri-scar region by PCR: $2 \times 10^6$ of mesenchymal stem cells at 95% transduction efficiency with the Ad5RSVLacZ vector (Gene Transfer Vector Core, University of Iowa) were suspended in a reconstituted solution of thrombin and fibrinogen to form the patch. The patch containing sMSCs that express the LacZ reporter gene was applied to the epicardial surface of the expected infarct area by means of a biological adhesive. At about 21 days post-transplantation, the patch and the peri-scar region of the left ventricle were resected for PCR analysis. DNA used as the template was extracted with a High Purity PCR Template Preparation Kit (Roche Molecular Biochemicals), Advan Taq plus DNA polymerase and 10×Advan Taq plus PCR buffer (Clontech) were used in the reaction system; PCR nucleotide mix (10 mM) was purchased from USB. The forward primer (5'-CAT-GCC-GAT-TGG-TGG-AAG-TAA-3' (SEQ ID NO:1)) was complementary to sequences of the RSV-LTR and was used to detect the RSV promoter in replication-deficient recombinant adenoviruses (Ad5RSVLacZ); the reverse primer (5'-AAA-GCG-CCA-TTC-GCC-ATT-3' (SEQ ID NO:2)) amplified a 150 nt LacZ gene fragment from Ad5RSVLacZ. The size of the PCR product from the RSVLTRLacZ amplification is about 0.56 Kb. The PCR reaction in 50 μl of volume was as follows: 100 ng DNA template, 5 μl 10× buffer, dNTP (2.5 mM each) 1 μl, Advan Taq plus 1 μl, forward primer 1 μl 10 μM, 1 μl 10 μM reverse primer, supplement $H_2O$ to 50 μl and set at 95° C. for 10 min for one cycle, and then 99° C. for 15 sec and 60° C. for 1 min for 35 cycles.

Example 7
Phenotype of sMSCs

The surface antigens CD44, CD45, HLA-Class I, and HLA-Class II were examined by flow cytometry using about $1.5 \times 10^5$ cells per 100 μl. Cells were labeled with primary monoclonal antibodies (mAbs, 2 μg each) directed against pig CD44, CD45, HLA-Class I and HLA-Class II antigens. Cells were incubated at 4° C. for 30 minutes and washed; the second polyclonal antibody-FITC conjugated against mouse IgG (1 μg/tube) was added and incubated at 4° C. for an additional 30 minutes. The mouse isotype IgG (2 μg) was added to $1.5 \times 10^5$ cells instead of primary mAbs for a negative control. The phenotype profiles of sMSCs were shown to be negative for CD45 and HLA-Class II, and positive for CD44 and HLA-Class I (FIG. 1). The thin line profiles represent mIgG-staining isotype as a control.

Example 8
Chondroblast and Osteoblast Differentiation from sMSCs

Figure 2:
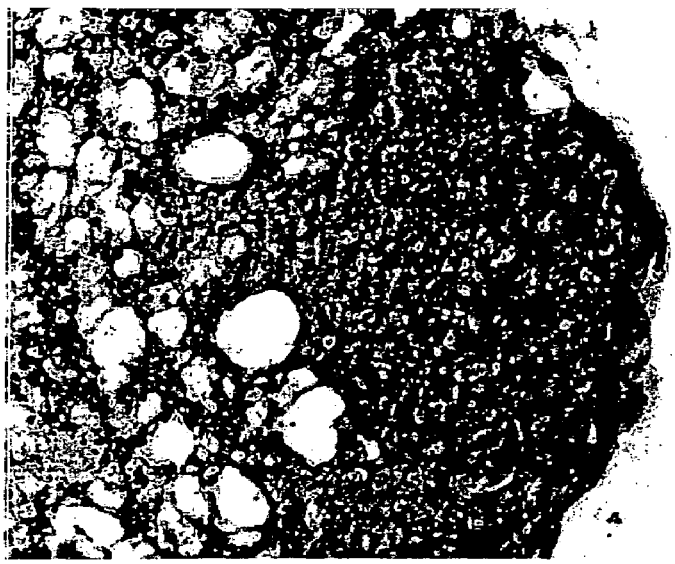
FIG. 2 shows the differentiation of sMSCs.
Figure 2:
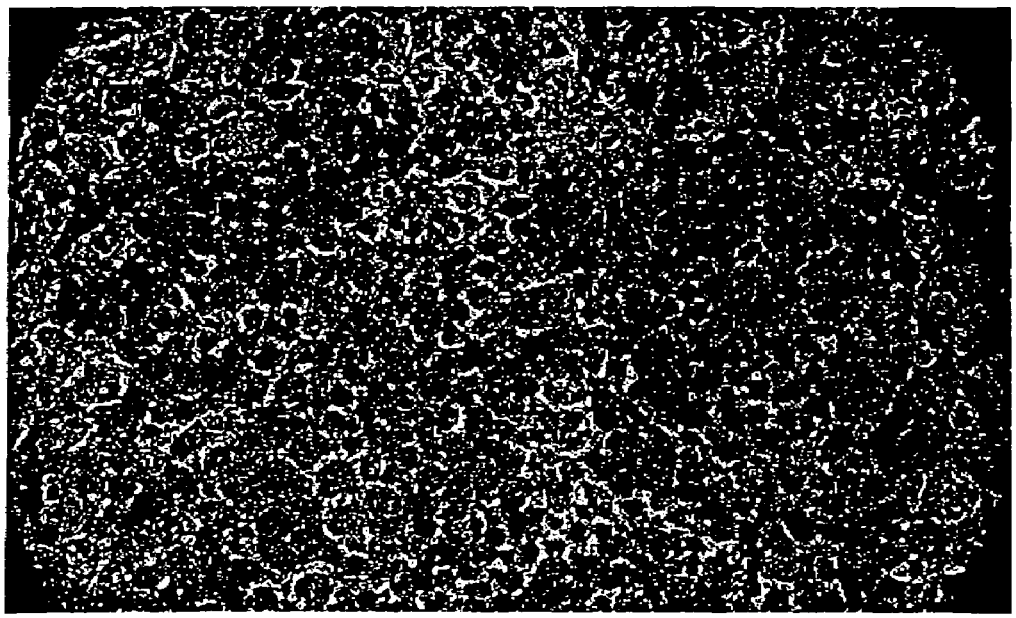
Figure 2:
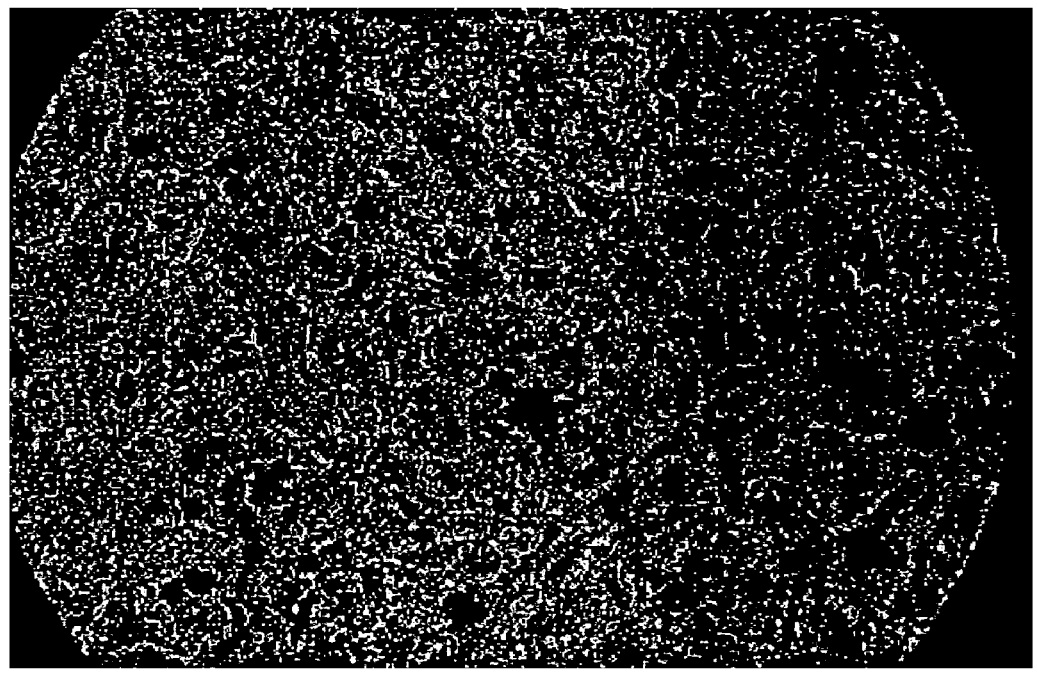

To demonstrate the pluripotency of MSCs, cells were cultured in conditions that have previously been reported to cause transformation of stem cells into chondroblasts or osteoblasts. sMSCs were trypsinized and aliquots of $25 \times 10^4$ cells in 0.5 ml chemically defined medium with porcine TGF-β (10 ng/ml) and dexamethasone $10^{-7}$ M were centrifuged in 15 ml conical tubes at 500×g. The pelleted cells were left at the bottom of the tubes and incubated in a $CO_2$ incubator. Within 24 hrs after incubation, the sedimented cells formed a spherical mass (an aggregate) at the bottom of the tube. The aggregate did not adhere to the tube wall. Differentiation to chondroblasts was shown by toluidine blue staining and type II collagen staining (FIG. 2A). When cell aggregates were cultured in chemically defined medium containing 0.05 μM dexamethasone but without TGF-β, toluidine blue staining revealed no evidence of cartilaginous matrix production.

Osteoblast differentiation: Trypsinized cells were plated onto 6-well plates at $3 \times 10^3$ cells/cm$^2$ in 10% serum DMEM medium. On the following day, the medium was replaced with fresh medium containing 100 μM dexamethasone (Sigma), 10 mM β-glycerophosphate (Sigma) and 50 μM ascorbic acid-2-phosphate (Sigma), with media changes every 3 to 4 days. On days 4, 8, 12, 16 and 20 of culture, samples were assayed for alkaline phosphatase activity (FIG. 2B) and mineral deposition (FIG. 2C) by histochemical staining with Sigma Kit 85 and the Von Kossa method, respectively (Pittenger et al., 1999, Science 284:143-147). After 8-14 days in osteogenic culture medium, over 80% of cells were alkaline phosphatase (Apase) positive. Calcium accumulation was shown after one week and increased over time (FIGS. 2B and 2C).

This chondroblast and osteoblast differentiation potential was maintained after sMSCs were transduced with the LacZ reporter gene.

Example 9
sMSC Transduction

Figure 3:
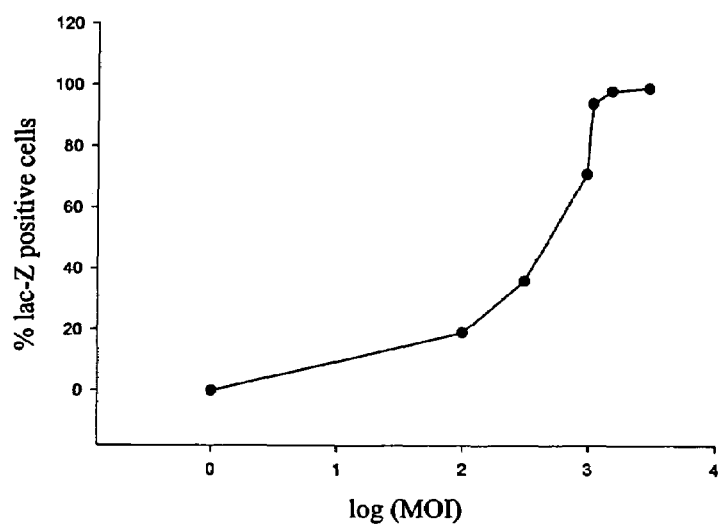
FIG. 3 shows transduction of sMSC by the recombinant adenovirus AdRSVlacZ.
Figure 3:
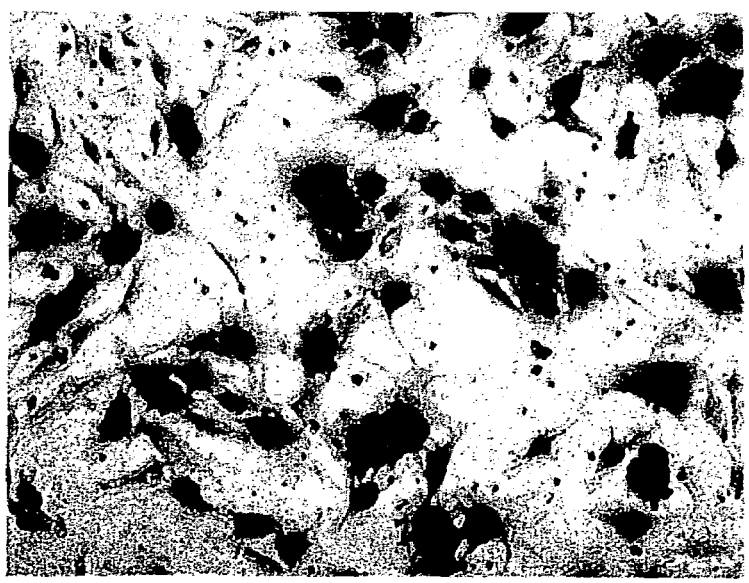

The labeling experiments revealed that sMSCs could be efficiently labeled by use of the recombinant adenoviruses Ad5RSVlacZ at high MOI. The maximum number of cells expressing β-galactosidase was achieved at 1500 to 2000 MOI (FIG. 3). Consequently, this concentration was used for labeling cells for patch transplantation experiments. Samples of transduced pMSCs were plated in T25 flasks and stained with β-gal to determine transduction efficiency (FIG. 3B). Some of the transduced sMSCs were maintained in culture to examine how long the cells continue to express β-galactosi dase. Results indicated that β-galactosidase is expressed for one to two months.

Example 10

MSC Patch

Figure 4:
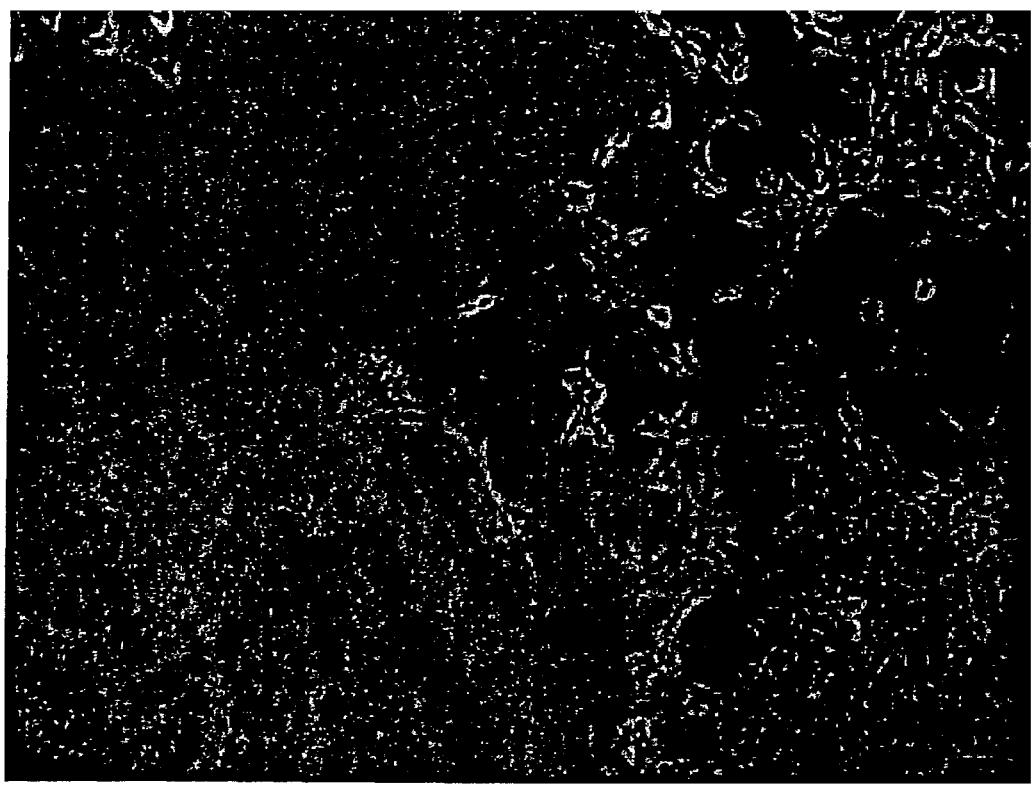
FIG. 4 shows a high power microphotograph of sMSC emigrating from a fibrin matrix after 2 days in culture.

In vitro MSC Patch: To examine cell behavior and proliferation potential within the fibrin matrix, equal volumes (5 ml) of the reconstituted fibrinogen and thrombin solution containing $2\times10^6$ cells were mixed and pooled into a 25 mm Falcon culture dish using the double syringe applicator described above. The mixture of cells was gelled for a few seconds and then overlaid with 3 ml of the stem cell medium; cultures were incubated at 37° C. in 5% $CO_2$/95% air and the medium was changed every two days. Using an inverted contrast microscope, it was possible to see cells entrapped in the fibrin gel and determine whether the cells had spread. A high power microphotograph of sMSCs emigrating from the fibrin matrix after 2 days in culture is illustrated in FIG. 4.

Figure 5:
FIG. 5 shows the in vivo use of an sMSC patch.
Figure 5:
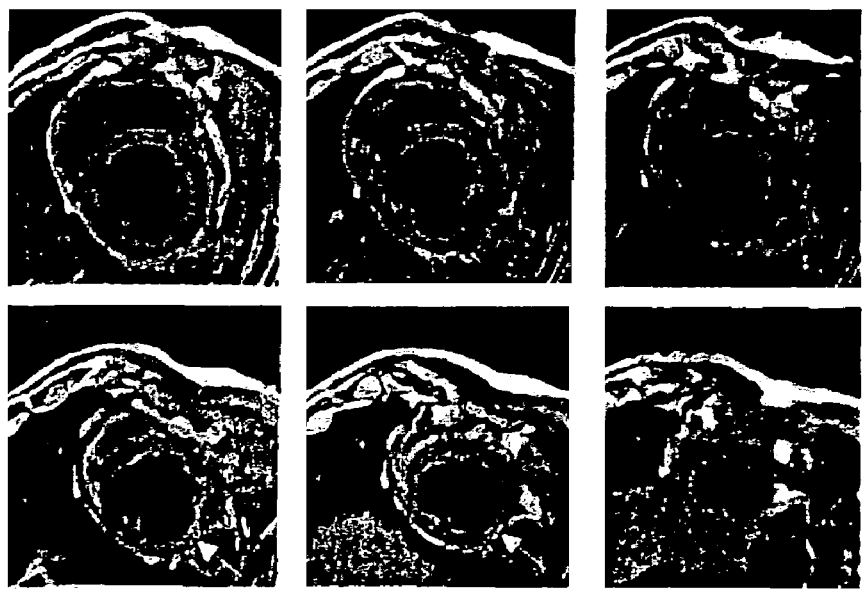
Figure 5:
Figure 5:
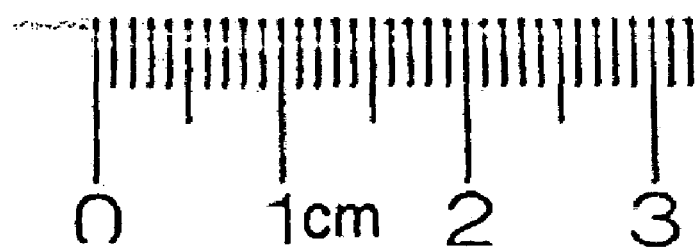
Figure 5:
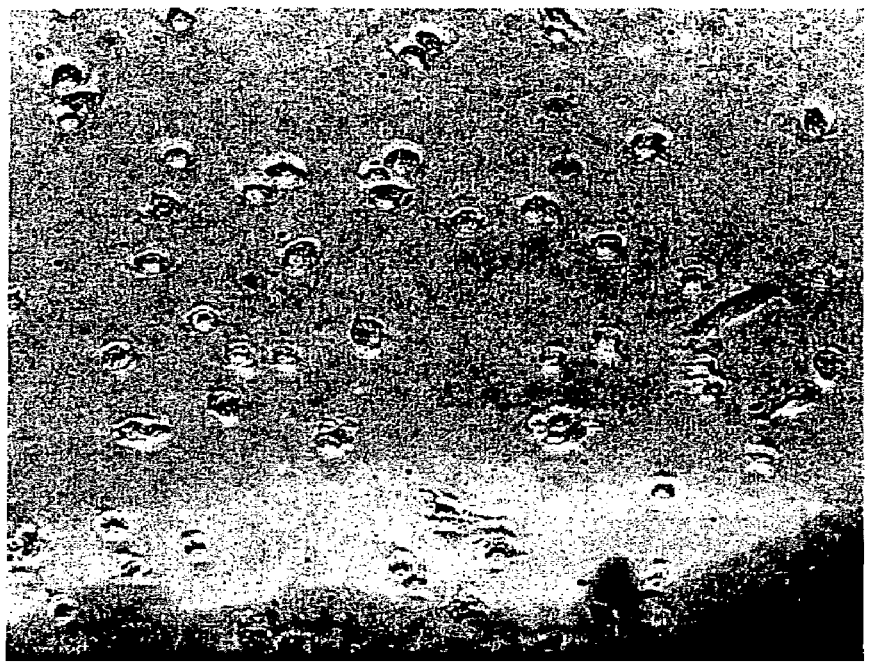
Figure 5:
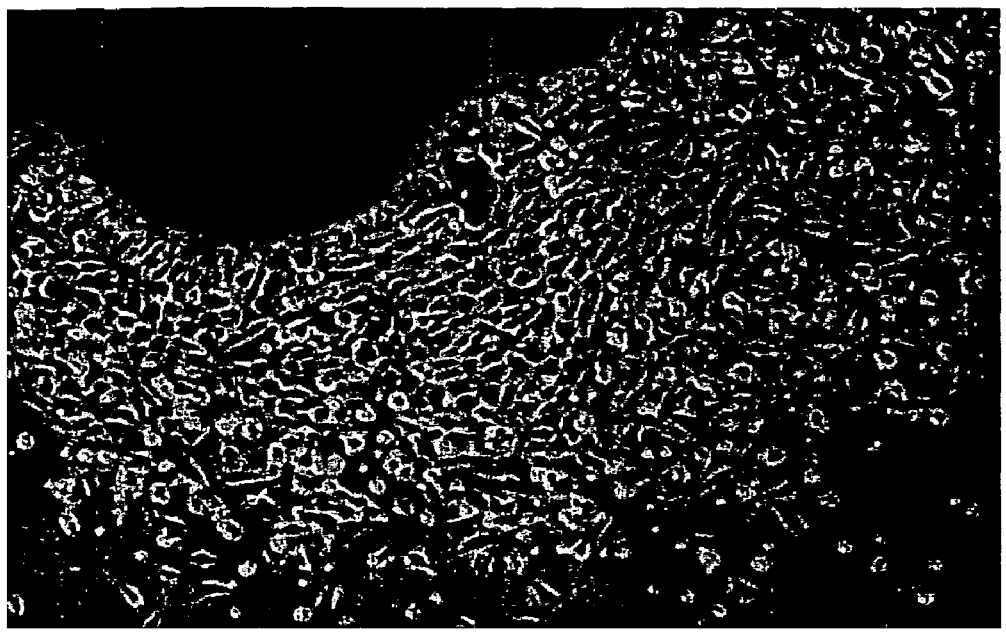
Figure 5:
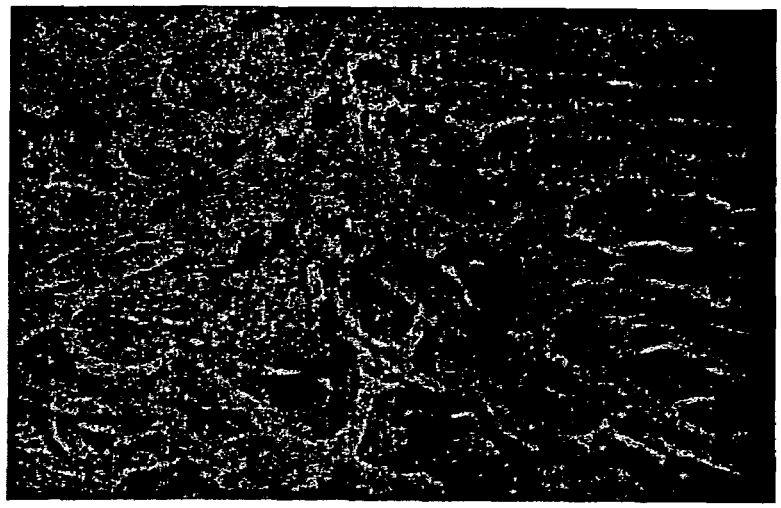
Figure 5:
Figure 5:
Figure 5:
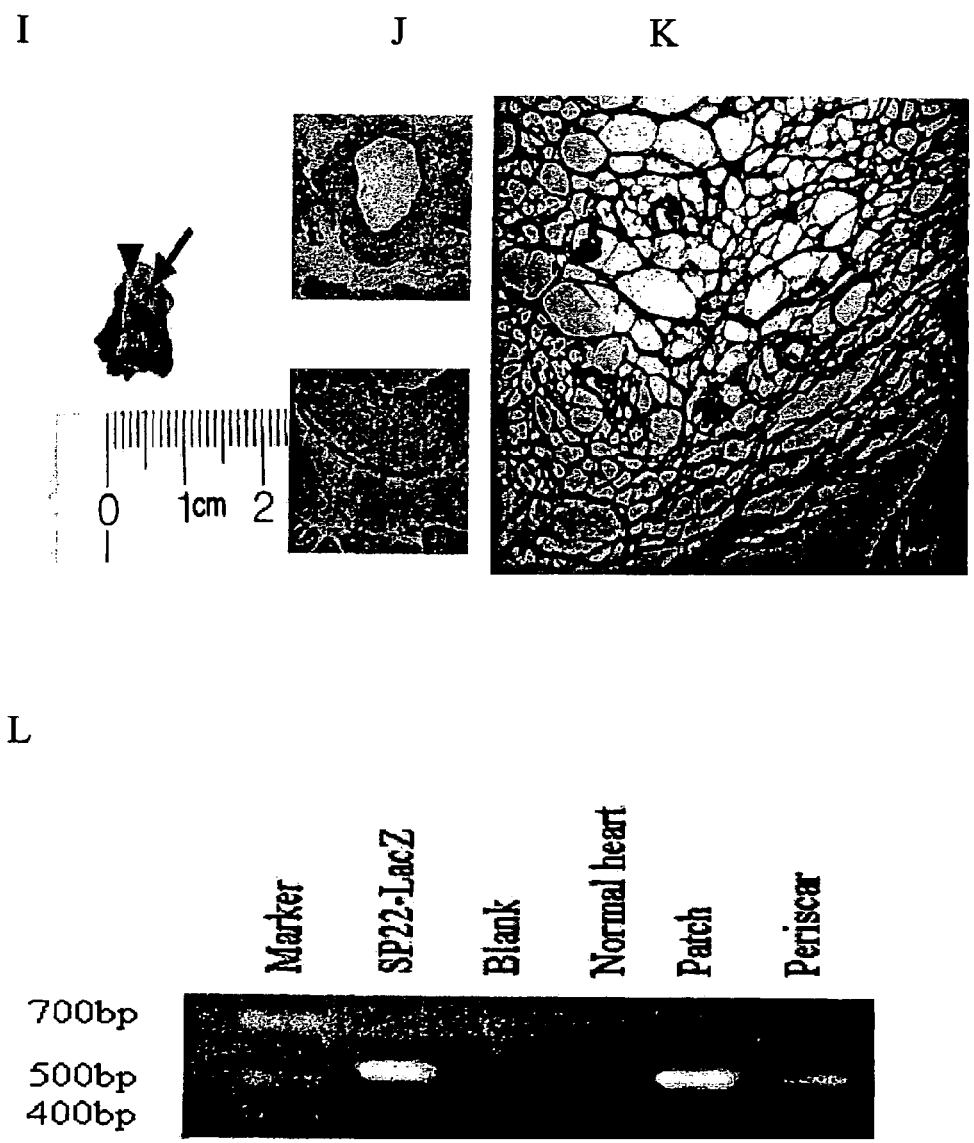

In vivo sMSC Patch: In vivo studies were performed in 3 groups of animals: Transplantation group (Tx, N=8), patch without stem cell group (P, N=6), and $1^{st}$ diagonal coronary artery ligation group (L, N=6). Studies were carried out to test whether the sMSCs delivered by a fibrin-patch would respond to the ischemic stimuli to migrate and home to the infarcted myocardium. Typical results from one study are illustrated in FIGS. 5A-I. FIG. 5A illustrates a fibrin MSC patch that was applied on the surface of the myocardial infarction produced by ligation of the $1^{st}$ diagonal coronary artery. FIG. 5B illustrates magnetic resonance images used to assess LV function. The MRI data indicated an increased LV wall thickness in the infarct zone of hearts with stem cell transplantation (Tx) (FIG. 5B) as compared to groups treated with the patch without cells (P) or coronary ligation (L) littermates. In hearts without postinfarction LV remodeling, the LV systolic thickening fraction was significantly improved in hearts with fibrin-stem cell patch transplantation (Table 1).

FIG. 5C illustrates X-Gal staining of a specimen with myocardial infarct and periscar area. sMSCs that express the β-galactosidase reporter gene are seen homing into the anterior LV wall (FIG. 5C). In stem cell culture medium, the "blue" cells migrated out of the specimens taken from the peri-scar area and continued to divide (FIG. 5D and 5E). These data indicate that the blue X-Gal color originated from live sMSCs.

Example 11

PCR, Tissue Staining and Microscopic Evaluations

Using the porcine model of postinfarction LV remodeling and immunohistochemical methods described herein, autologous sMSCs were found to home into the necrotic myocardium and differentiate into myocytes as evidenced by cardiac-specific troponin T staining (FIGS. 5G and 5H). Light microscope (LM) evaluation indicated that the transplanted autologous "blue" cells had survived and differentiated into new myocytes in the peri-scar region (FIGS. 5F, 5G, and 5H). FIG. 5I illustrates a pathologic specimen that includes the interface between the fibrin patch (shown in pale white) and the injured myocardium (shown in red). A new vessel growing into the patch is readily seen in FIG. 5J. FIG. 5K shows immunohistochemical staining of the interface between the patch and the peri-scar region. Rich neovascularization in the scaffold of the patch area clearly is seen (FIG. 5K). These data indicate that this biodegradable stem cell patch stimulates neovascularization.

PCR amplification of specimens taken from the "blue" area indicated the presence of Ad5RSVLacZ nucleic acid (FIG. 5L). This was not seen in hearts of patients assigned to the P or L groups.

Example 12

Calculated Efficiency of Stem Cells Homing into the Ischemic Myocardium

Twelve biopsy specimens (1 $mm^3$ each) from necrotic and border zones were taken from each LV, and placed into T25 flasks for culture using stem cell culture medium. Twenty-four hours later, X-Gal staining was performed and "blue cells" were counted. The total number of stem cells that migrated out of the ischemic myocardium was obtained relative to the volume of the biopsy specimen (weight×1.06 as the density of myocardium); data represent the mean of 8 counts of specimens from each heart. The identical specimen collection and culture procedure was also performed in areas remote from the infarct in hearts in P and L groups. No blue cells were found from the cultured specimens of the P or L hearts. The homing efficiency was calculated as follows: efficiency (%)=100×total number of cells migrated into the LV/number of stem cells transplanted. Counting the "blue" cells in the infarcted area (including the peri-scar zone) indicated that about 10% of the transplanted cells migrated to the myocardial infarct. However, only a small portion of sMSCs that reached the peri-scar myocardium differentiated to myocyte-like cells (FIGS. 5F, 5G, and 5H). MRI was used to evaluate LV contractile performance, and a significant improvement of LV contractile function was observed in hearts that received MSC transplantation.

Example 13

PEGylated Fibrin Patch

A PEGylated fibrin patch for MSCs transplantation was developed by modifying fibrinogen with the benzotriazole carbonate derivative of PEG (BTC-PEG-BTC). BTC-PEG-BTC has electrophilic groups at both ends that can react with protein amino groups, producing stable urethane (carbamate) linkage. Utilizing reactive PEG, the number of crosslinks between adjacent fibrin monomer molecules can be increased and/or growth factors can be covalently attached to the fibrin.

The chemical PEGylation of fibrinogen was verified by both amine group quantification and SDS-PAGE using a double staining technique with Coomassie Brilliant Blue R-250 and iodine.

The physical properties and clotting characteristics of the fibrin patch and the PEGylated fibrin patch were compared using various molar ratio combinations of PEG to fibrinogen (PEG:fibrinogen). After seeding with porcine MSCs, the cell viability in the different patches was examined. The data indicate that the degree of modification can be controlled by varying the molar ratio of PEG to fibrinogen. The clotting time increased significantly in proportion to the molar ratio up to 5:1. At the molar ratio of 10:1, although the gelation time of PEGylated fibrin patch increased approximately 10% (18±0.3 min versus 15±0.6 min) compared to the fibrin patch, the MSCs viability 2 days after loading increased significantly.

These results indicate that although the PEGylated fibrin patch may take slightly longer to gel, the PEGylated fibrin provides a healthy and stable environment for MSCs.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims

What is claimed is:

1. A method of delivering stem or progenitor cells to infracted myocardial tissue of a mammal comprising depositing, onto or in the vicinity of a surface of said infracted myocardial tissue of said mammal, a PEGylated fibrinogen solution comprising said cells and at least one growth factor, wherein said growth factor is covalently bound to said PEG.

2. The method of claim 1, wherein said stem or progenitor cells are bone marrow cells.

3. The method of claim 2, wherein said bone marrow cells are autologous to said mammal.

4. The method of claim 1, wherein fibrinogen in said PEGylated fibrinogen solution is autologous to said mammal.

5. The method of claim 1, further comprising introducing a fibrinogen-converting agent to said PEGylated fibrinogen solution.

6. The method of claim 5, wherein said fibrinogen-converting agent is a serine protease.

7. The method of claim 6, wherein said serine protease is thrombin.

8. The method of claim 7, wherein said thrombin is autologous to said mammal.

9. The method of claim 5, wherein said fibrinogen-converting agent is added to said PEGylated fibrinogen solution before said depositing.

10. The method of claim 5, wherein said fibrinogen-converting agent is added to said PEGylated fibrinogen solution after said depositing.

* * * * *

UNITED STATES PATENT AND TRADEMARK OFFICE
CERTIFICATE OF CORRECTION

| | | |
|---|---|---|
| PATENT NO. | : 7,442,397 B2 | Page 1 of 1 |
| APPLICATION NO. | : 10/874449 | |
| DATED | : October 28, 2008 | |
| INVENTOR(S) | : Jianyi Zhang | |

It is certified that error appears in the above-identified patent and that said Letters Patent is hereby corrected as shown below:

Column 1, line 3, please insert

--STATEMENT REGARDING FEDERALLY FUNDED RESEARCH

This invention was made with government support under National Institutes of Health Grant Numbers HL50470, HL61353, and HL67828. The federal government has certain rights in the invention.--

Column 1, line 10, please delete "60/337,148" and insert --60/377,148-- therefor.

Signed and Sealed this

Tenth Day of March, 2009

JOHN DOLL
*Acting Director of the United States Patent and Trademark Office*

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide

<400> SEQUENCE: 1
catgccgatt ggtggaagta a            21

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide

<400> SEQUENCE: 2
aaagcgccat tcgccatt            18